United States Patent

Bouquet De La Joliniere et al.

[11] Patent Number: 5,989,265
[45] Date of Patent: Nov. 23, 1999

[54] DEVICE FOR PINPOINTING SUSPECT LESIONS OF THE BREAST AND APPARATUS FOR POSITIONING IT

[76] Inventors: Jean Henri Bouquet De La Joliniere, 14 rue Henri-Regnault, F-92150 Sureanes, France; Alexandre Worcel, 36 rue de Pommard, F-75012 Paris, France

[21] Appl. No.: 08/913,081
[22] PCT Filed: Mar. 7, 1996
[86] PCT No.: PCT/FR96/00355
    § 371 Date: Dec. 22, 1997
    § 102(e) Date: Dec. 22, 1997
[87] PCT Pub. No.: WO96/27328
    PCT Pub. Date: Sep. 12, 1996

[30] Foreign Application Priority Data

Mar. 8, 1995 [FR] France ................................... 95/02722

[51] Int. Cl.$^6$ .................................................. A61B 17/00
[52] U.S. Cl. .......................................................... 606/116
[58] Field of Search ..................................... 606/116, 108, 606/180, 185; 604/164–166, 167–169, 170, 181, 185

[56] References Cited

U.S. PATENT DOCUMENTS

| | | |
|---|---|---|
| 4,592,356 | 6/1986 | Gutierrez . |
| 4,616,656 | 10/1986 | Nicholson et al. ................. 604/164 X |
| 5,059,197 | 10/1991 | Urie et al. ................................ 606/116 |
| 5,158,084 | 10/1992 | Ghiatas . |
| 5,205,829 | 4/1993 | Lituchy ..................................... 604/164 |
| 5,221,269 | 6/1993 | Miller et al. ........................ 604/164 X |
| 5,409,004 | 4/1995 | Sloan . |
| 5,685,853 | 11/1997 | Bonnet ..................................... 604/164 |

FOREIGN PATENT DOCUMENTS

| | | |
|---|---|---|
| 88/06864 | 9/1988 | WIPO . |
| 90/15576 | 12/1990 | WIPO . |

*Primary Examiner*—Michael Buiz
*Assistant Examiner*—Vikki Trinh
*Attorney, Agent, or Firm*—Burns, Doane, Swecker & Mathis, L.L.P.

[57] ABSTRACT

Device for pinpointing lesions detected in a breast comprising an anchoring means comprising one or more flexible and elastic elements which are capable of assuming a linear form during positioning and of deforming once in place, and at least one wire of a length which is at least equal to a depth of implantation of the anchoring means within the breast.

17 Claims, 2 Drawing Sheets

DEVICE FOR PINPOINTING SUSPECT LESIONS OF THE BREAST AND APPARATUS FOR POSITIONING IT

BACKGROUND OF THE INVENTION (i) Field of the Invention

The present invention relates to a device which can be used in surgery, and more particularly to a device for pinpointing small suspect lesions of the breast, such as micro-calcifications, with a view to their optimized ablation by surgical means, as well as to an apparatus for positioning it.

(ii) Description of Related Art

Screening for breast cancers is normally done by mammography, since this technique permits detection of lesions of small dimensions, such as micro-calcifications. It is then necessary to remove tissues from the mammary gland in order to analyze them and verify their possible cancerous nature. This removal is generally done by surgical means, or by biopsy, or else by needle puncture.

The practitioner (surgeon) normally pinpoints the suspect lesions on mammography images by taking the nipple of the breast as a reference point, and uses the frontal and profile measurements in order to determine approximately the position of the lesion from which a sample is to be taken.

One of the main difficulties encountered by practitioners is that of locating the lesion which has been detected by mammography. This is because the position of the breast is very different during mammography (frontal and profile), where the patient is in a seated position, the breast pressed between two plates, and during the operating phase where the patient is generally lying on her back on an operating table.

The result of this is that the mammography reference markers do not correspond precisely to the actual position of the lesion during the removal operation, regardless of whether this is done by surgery, by biopsy or by puncture. Now, the lesions consisting of micro-calcifications are often incipient and noninvasive cancers of small dimensions, the diameter of which is of the order of magnitude of millimeters and does not exceed 1 cm. These lesions do not present any particular consistency or coloration. Pinpointing them is therefore difficult, even after mammography from several angles, for example frontal and profile.

In practice, the surgeon is forced to make an estimate and remove a relatively large volume of breast tissue susceptible of containing the suspect lesion. The sample removed is then checked by X-ray to verify the presence of the micro-calcifications, and then analyzed on the spot by a specialist (anatomical pathologist).

Despite all the precautions taken during these operations, it is very often discovered, subsequently, that there are micro-calcifications still remaining in the breast. These micro-calcifications are detected during mammographs performed several weeks after the operation described hereinabove. It is then often necessary to perform another operation.

Because of these difficulties, and in order to avoid having to perform several operations in succession, the surgeon is compelled to remove much greater quantities of tissue than would be necessary if the lesions detected by mammography could thereafter be pinpointed with good reliability and satisfactory precision. Moreover, the surgeon cannot be certain that all the micro-calcifications have been removed other than by broadening the ablation of tissues excessively, which can additionally have a considerably adverse esthetic and psychological impact on the patient.

Various devices have been proposed in an attempt to overcome these difficulties. For example, patent FR-A-2,660,545 describes biopsy equipment in association with mammography from two angles with the aid of a rotating head taking the images, this equipment being intended to locate suspect lesions corresponding to incipient cancers. However, this equipment is complex and its use is not very convenient for the patient.

Patent FR-A-2,666,217 describes a device for stereotaxic pinpointing and puncturing of a lesion of small dimensions, detected by mammography, by means of a trocar or needle for aspiration biopsy. This device is designed to permit two X-ray images to be taken from two different angles, the patient's breast being pressed between two plates, one of which includes a zone for access to the breast, as well as a support for vertical guidance of a puncture needle, the movement of which is determined as a function of the results of the detection of the lesion using the mammography images. This device necessitates immobilizing the patient's breast between the two plates, not only during the mammography, but also during the operation of puncturing and analysis of the removed sample, that is to say for a prolonged period of time, which is not conducive to the patient's comfort.

Patent U.S. Pat. No. 5,158,084 describes a device for pinpointing lesions in a tissue, comprising a flexible radio-paque wire having at least two markers which are detectable by palpation and which are intended to allow the surgeon to determine the position of the end of the wire without needing to trace it in its entirety.

Patent U.S. Pat. No. 4,592,356 describes an anchoring device for biopsy, comprising a needle whose point is in the form of a double hook and whose rod includes threading for the positioning of a blocking piece against the surface of the skin.

Patent application WO-A-90/15576 describes an apparatus for positioning a pinpointing device, comprising an anchoring means of helical shape fixed on a rod which is capable of being set in rotation inside a hollow needle for the purpose of inserting the anchoring means in the tissues.

SUMMARY OF THE INVENTION

The present invention relates to a device for pinpointing a suspect lesion of small dimensions, such as a micro-calcification, making it possible to pinpoint the lesion with certainty and precision after detection in the breast by mammography, in such a way as to permit subsequent puncturing, biopsy or surgical ablation, without the risk of inaccuracy in locating the lesion.

The invention also relates to an apparatus for positioning the pinpointing device hereinabove.

The device according to the present invention, for pinpointing lesions of small dimensions detected in the breast by mammography, is distinguished by the fact that it comprises an anchoring means consisting of one or more flexible and elastic elements which are capable of assuming a linear form during positioning and of deforming once in place in the breast tissues, as well as at least one wire of a length which is at least equal to the depth of implantation of the anchoring means within the breast.

The anchoring means and the wire which is fixed to it may advantageously be made of a radioparent material, or by contrast of a radiopaque material, depending on the conditions sought for the subsequent operation of puncturing, biopsy or surgical ablation.

Figure 1:
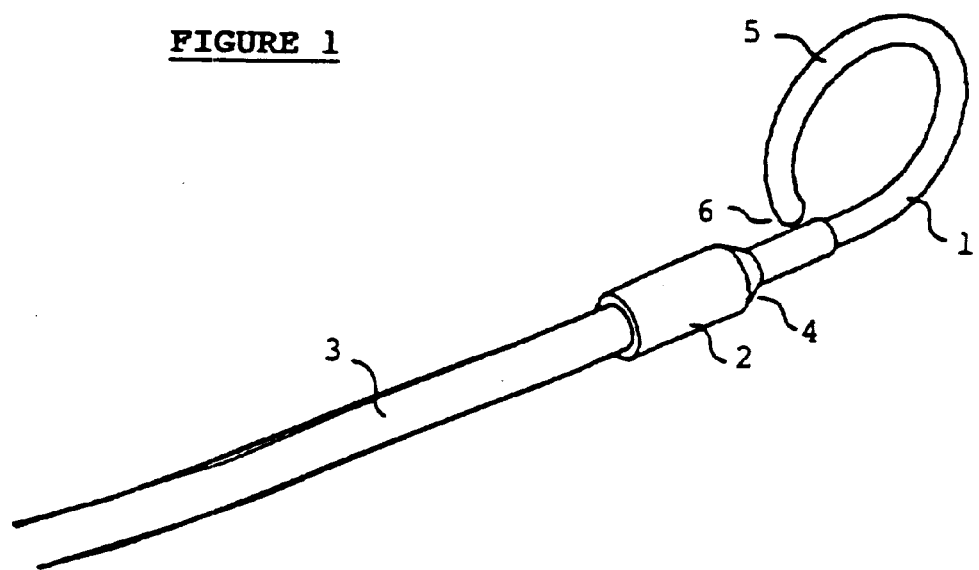
FIG. 1 shows a perspective view of an anchoring means made of superelastic material, according to the invention.

The apparatus for positioning the pinpointing device according to the present invention comprises, in combination, a hollow needle or trocar of a length at least equal to the depth of implantation of the anchoring means within the breast, a rod engaging in the needle of the trocar and pushing back the anchoring means capable of passing through the conduit of the trocar, on which means at least one wire is fixed, as well as a removable blocking piece disposed between the base of the trocar and the base of the rod.

In accordance with the invention, the length of the rod is substantially equal to the length of the needle, and the height of the removable blocking piece is preferably approximately equal to the length of the blocking means of linear form in the folded-up position. Thus, the rod, once engaged in the hollow needle of the trocar, leaves, at the end of this needle, a space which corresponds to the length of the anchoring means. When the blocking means is removed, the rod can be engaged totally in the needle of the trocar, and it pushes the anchoring means back out of the conduit of the needle, which anchoring means can open out by virtue of the flexibility and elasticity of the material used for producing it. The base of the rod of the trocar is provided with a shoulder cooperating with the blocking piece to make it easier to hold it.

As was indicated hereinabove, the anchoring means is made of a flexible and elastic material, preferably radioparent, which is capable of changing from a linear form when folded up to a deployed form occupying a defined spatial configuration.

In the folded-up form, the anchoring means is of a cylindrical form overall, and of a diameter substantially equal to the internal diameter of the conduit of the needle of the trocar. It can be kept in this linear, folded-up form by means of a simple cylindrical sleeve, for example to facilitate its introduction into the needle of the trocar. The total diameter of the anchoring means when folded up is between 1 and 3 mm approximately, and its length is between 2 and 30 mm.

In the deployed form, the anchoring means can be single-stranded and curvilinear, in the form of an arc of a circle or of a hook, or multi-stranded, each strand occupying a different spatial direction. The maximum dimension of the anchoring means, once deployed, is approximately 3 to 10 mm.

The material used for producing the anchoring means can be chosen from among the materials which are acceptable in the surgical domain and which are compatible with the breast tissues in which they are temporarily implanted. Moreover, they must have a flexibility and elasticity sufficient to change from the folded-up form to the deployed form, as was indicated hereinabove. The material is preferably chosen from among the biocompatible radioparent materials which possess the characteristics hereinabove. A nonionizing material may advantageously be chosen to facilitate certain analyses (MRI).

It will be possible, for example, to use anchoring means which are made of polyethylene or of a nickel/titanium alloy with superelastic action, of a shape-memory polymer, or of an organic or metal alloy with shape memory.

For example, it may be advantageous, according to the present invention, to use an anchoring means consisting of a single elastic strand with shape memory, or of several coaxial, elastic and flexible strands which are capable of spacing apart from one another.

According to a preferred embodiment, the point of the needle is beveled. The result of this is that the anchoring means, preferably in the form of a single strand, folds up progressively once its distal end is situated level with the bevel of the point of the needle.

Fixed at the base of the anchoring means there is a wire made of a material which can be radioparent or radiopaque. According to one embodiment, this wire is fixed via one of its ends to the base of the anchoring means, and in this case only one strand of the wire is accessible. According to one variant, the wire passes through a ring provided at the base of the anchoring means, thereby forming two strands, and the two ends of the wire are then accessible. This wire serves essentially to facilitate locating the anchoring means implanted in the breast tissues.

The wire can be made, for example, of biocompatible polyester of a type available on the market, for example Ticron® or Dacron® (siliconized polyester braids).

According to an advantageous embodiment, the apparatus for positioning the pinpointing device according to the invention includes a crimping ring disposed at the base of the needle of the trocar, so as to make it easy to join the anchoring means and the wire by simple crimping using a pincer or punch.

The functioning of the device according to the present invention is extremely simple: the anchoring means, folded up in a linear form, is placed in the conduit of the needle of the trocar, the rod is engaged in the conduit of the trocar in such a way as to push the anchoring means back, and, at the same time, the removable blocking piece is put in place in such a way as to limit the engagement of the rod and to prevent it from expelling the anchoring means from the conduit of the needle; then, operating under X-ray monitoring, the practitioner (radiologist) uses one hand to introduce the trocar into the breast until the point is at the center of the lesion, then, using the other hand, removes the removable blocking piece locking the mechanism, and, pressing on the base of the rod forming a plunger, injects the anchoring piece previously introduced into the rod of the trocar. On emerging from the end of the conduit, the anchoring piece deforms by virtue of its flexibility and fixes in the breast tissues.

In practice, the anchoring means and the wire which is fixed to it, and the rod and the blocking means, are positioned in the needle of the trocar prior to the use of the apparatus according to the invention, the anchoring means being situated at the needle end, ready to be injected into the breast tissues by the practitioner.

The trocar and the rod are then removed and the only things remaining in the breast are the anchoring means and the wire made of radioparent material, the end of which, protruding outside the breast, can be cut off. A sterile and hermetic dressing can then be applied.

This anchoring means serving as a marker can remain in place in the breast for several days, until the surgical intervention for ablation of the lesion. Thus, the pinpointing of the lesion within the breast, in order to permit its ablation, no longer depends on the position of the breast. The ablation can then be limited precisely to the lesion, which simplifies the surgical operation. The radioparent anchoring and pinpointing means is easily removed during the surgical operation for ablation of the lesion.

When the anchoring means and the wire are made of radioparent material, it is possible to carry out complementary mammographs without difficulty, should this prove necessary.

Moreover, the device according to the present invention can be used without it being necessary to resort to complex and expensive equipment, other than the mammography apparatus, which can be of the usual type and which it is not necessary to modify.

In contrast to the traditional devices of the state of the art, the device of the invention can be manipulated with just one hand, once the blocking piece has been removed, which considerably facilitates the precise positioning of the anchoring means near the lesion.

Finally, the device of the invention can be used for pinpointing other lesions which are capable of being detected in other soft tissues.

The examples described hereinafter illustrate the invention in greater detail, without limiting its scope, with reference being made to the attached drawings, As is represented in FIG. 1, the anchoring means consists of a strand (1) adopting a curvilinear form when it is not held in the needle of the trocar. At the base of the anchoring means (1) there is a sleeve (2) in which a wire (3) protruding rearward is crimped.

Figure 4:
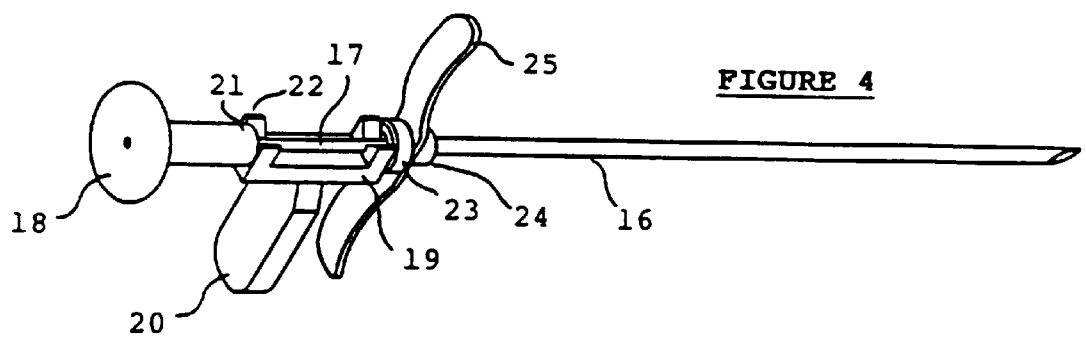
FIG. 4 shows a perspective view of a trocar equipped with a removable blocking piece, for implantation of the anchoring means.

The sleeve (2) includes a frustoconical head (5 [sic]) facilitating its positioning at the base of the needle of the trocar represented in FIG. 4.

The strand (1) includes a part (5) in the form of an arc of a circle of at least 270°, and a pointed end (6) facilitating its penetration into the breast tissues. It is made of nickel/titanium alloy with superelastic action. In the conduit of the needle of the trocar, is assumes a linear form adapted to the internal form of the conduit, and, on emerging from the needle, when it is pushed back by the rod of the trocar, it folds up into an arc of a circle approximately 8 mm in diameter. This form affords a resistance which is sufficient to ensure that the anchoring means is not displaced in the breast tissue as a function of the movements of the patient's body.

Figure 2:
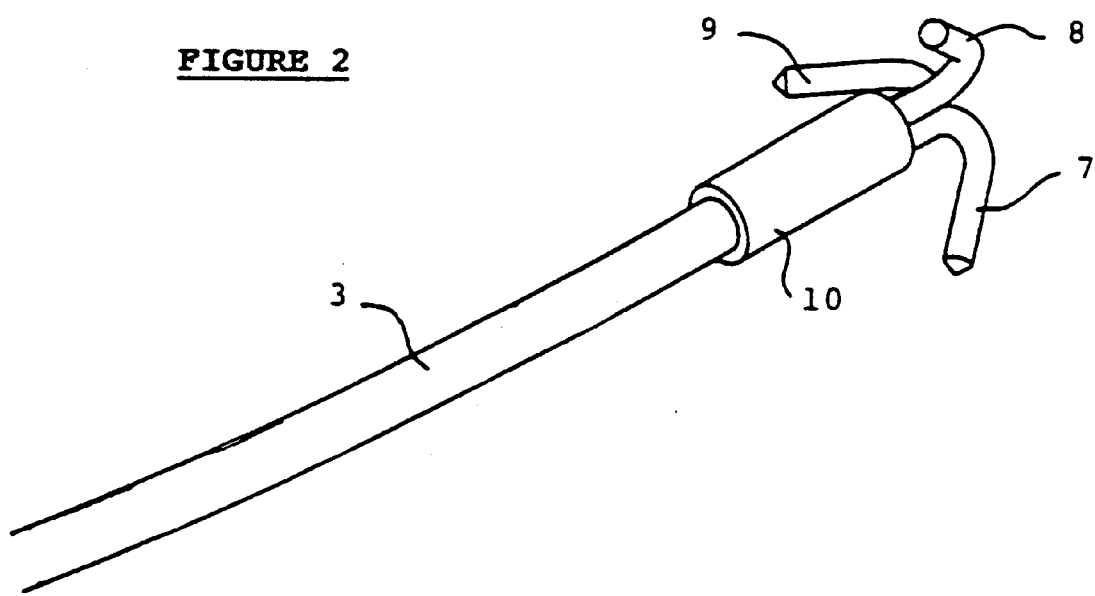
FIG. 2 shows a perspective view of another anchoring means according to the invention.

The anchoring means represented in FIG. 2 includes three elastic, flexible strands (7, 8 and 9) which are attached via their base by means of crimping in the sleeve (10).

These three strands, once deployed on emerging from the needle of the trocar, have a hook shape, the planes containing each of these hooks forming between them an angle of approximately 120°.

The wire (3) emerges at the rear of the crimping sleeve (10) at the base of the three strands (7, 8 and 9).

Figure 3:
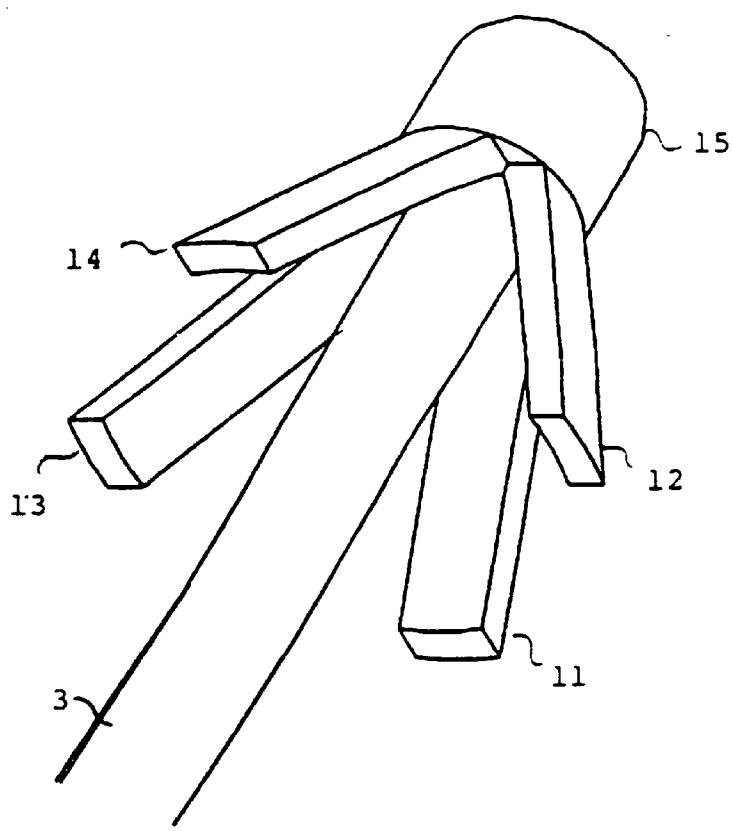
FIG. 3 shows a view of a variant of the anchoring means in FIG. 2.

The anchoring means represented in FIG. 3 is a variant of the one in FIG. 2, including four tongues (11, 12, 13 and 14) which are joined by their top being secured to a cap (15) and are capable of spacing apart from one another by pivoting relative to their top.

The diameter of the cap (15) corresponds to the internal diameter of the conduit of the needle of the trocar. Its shape is profiled in order to promote its penetration into the tissues.

In the normal position, the bases of the four tongues are spaced apart from one another. The flexibility and elasticity of the material used makes it possible to close them together so as to introduce them into the conduit of the needle, and, as soon as they emerge from the needle, they space apart again by virtue of their elasticity.

The wire (3), represented in FIG. 3, is attached to the base of the tongues, as in the preceding example, by crimping.

The apparatus in the cap for positioning the anchoring means is represented in FIG. 4.

The apparatus consists of a trocar including a hollow needle (16) into which it is possible to engage a rod (17) which is driven into the conduit of the needle by pressing on the pusher (18) until it comes into abutment against the removable blocking piece (19) which can be put in place and removed by acting on the handle (20). A shoulder (21) on the base of the rod (17) facilitates the positioning of the blocking piece (19) by cooperating with the bearing faces (22).

When the blocking piece (19) is removed, it is possible to press on the pusher (18) in order to cause the rod (17) to penetrate into the conduit of the needle (16) until the shoulder (21) comes into contact with the disk (23) of the crimping ring (24).

The handle (25) integral with the needle (16) makes it easier to manipulate the assembly.

We claim:

1. Device for pinpointing lesions detected in a breast comprising:
   an anchor comprising one or more flexible and elastic elements which are deformable to a linear form and returning by a shape memory to a substantial hook shape, and
   at least one wire different from and attached to the anchor and of sufficient length for implantation of the anchor within the breast.

2. Device according to claim 1, wherein the anchor and the wire are made of a radioparent material.

3. Device according to claim 1, wherein the anchor and the wire are made of a radiopaque material.

4. Device according to claim 1, wherein the elements are made of a nickel/titanium alloy.

5. Device according to claim 1, wherein the wire is made of polyester.

6. Device for pinpointing lesions detected in a breast, comprising:
   an anchor comprising a plurality of flexible and elastic strands; and
   a wire different from and attached to the strands at first ends of the strands and of sufficient length for implantation of the anchor within the breast;
   wherein the strands are substantially parallel to one another and to the wire at first ends of the strands, second ends of the strands being hook-shaped and spaced apart from one another, and the second ends of the strands being deformable to a folded position in which the second ends are substantially adjacent and are substantially parallel to the first ends of the strands and the wire.

7. Device according claim 1, wherein the anchor is held in a linear, folded-up position by a cylindrical sleeve.

8. Device according to claim 6, wherein the strands have a shape memory.

9. Device according to claim 6, wherein the strands are made of a nickel/titanium alloy.

10. Device according to claim 6, wherein the wire is made of polyester.

11. Apparatus for positioning a pinpointing device comprising:

- a pinpointing device for pinpointing lesions detected in a breast, the pinpointing device including an anchor comprising one or more flexible and elastic elements which are deformable to a linear form and returning by a shape memory to a substantial hook shape. and at least one wire different from and attached to the anchor and of sufficient length for implantation of the anchor within the breast;
- a hollow needle into which the anchor is capable of passing, the hollow needle being of a length at least equal to the depth of implantation of the anchor within the breast,
- a rod engaging in the hollow needle and pushing back the anchor, the at least one wire being fixed to the rod; and
- a removable blocking piece disposed between a base of the hollow needle and a base of the rod.

12. Apparatus according to claim 11 wherein the base of the rod of the hollow needle is provided with a shoulder cooperating with the blocking piece.

13. Apparatus according to claim 11 wherein the rod and the hollow needle have lengths which are substantially equal and wherein the blocking piece has a height which is approximately equal to a length of the one or more elastic elements in a linear, folded-up position.

14. Apparatus according to claim 11, further comprising a crimping ring disposed at the base of the hollow needle.

15. Apparatus according to claim 11, wherein the hollow needle has a point which is beveled.

16. Apparatus according to claim 11, wherein the elements are made of a nickel/titanium alloy.

17. Apparatus according to claim 11, wherein the wire is made of polyester.

* * * * *